United States Patent [19]

Abraham

[11] 4,265,253

[45] May 5, 1981

[54] SKIN CONDUCTING ELECTRODE AND ELECTRODE ASSEMBLY

[75] Inventor: William W. Abraham, New Hartford, N.Y.

[73] Assignee: Consolidated Medical Equipment Inc., Utica, N.Y.

[21] Appl. No.: 55,812

[22] Filed: Jul. 9, 1979

[51] Int. Cl.³ .............................................. A61N 1/18
[52] U.S. Cl. .................................... 128/798; 128/803
[58] Field of Search ............................... 128/639–641, 128/644, 783, 791–793, 798, 802, 803, 303.13

[56] References Cited

U.S. PATENT DOCUMENTS

| 3,565,059 | 2/1971 | Houser et al. | 128/640 |
| 3,817,252 | 6/1974 | Maurer | 128/798 |
| 3,977,392 | 8/1976 | Manley | 128/641 |
| 4,102,331 | 7/1978 | Grayzel et al. | 128/640 |

FOREIGN PATENT DOCUMENTS

| 1008135 | 4/1977 | Canada | 128/644 |
| 122258 | 2/1972 | Denmark | 128/641 |
| 1519782 | 8/1978 | United Kingdom | 128/640 |

OTHER PUBLICATIONS

Albisser et al., "Atraumatic Electrodes . . . Monitoring", JAAMA, vol. 5, No. 2, Mar.-Apr., 1971.

Primary Examiner—Lee S. Cohen
Attorney, Agent, or Firm—Larson, Taylor and Hinds

[57] ABSTRACT

A disposable skin conducting electrode assembly and electrode is disclosed for use on a patient wherein the electrode assembly comprises a gel pad, an electrode and an adhesive pad. The electrode is a thin conductive wire having a non-linear configuration such that the electrode extends across a width of skin substantially greater than the width of the wire. In one particular embodiment, the wire is in a saw-toothed configuration. The gel pad covers one side of the conductive wire, and the adhesive pad covers not only the other side of the conductive wire but the gel pad as well. The adhesive pad is used to hold the electrode assembly to the skin of the patient. A lead wire, connected at one end to the conductive wire, is provided to connect the electrode assembly to a suitable source of electric impulses. The electrode assembly may be used where any electrode is usable but has particular application for transcutaneous electrical nerve stimulation or as a post-operative electrode.

5 Claims, 5 Drawing Figures

SKIN CONDUCTING ELECTRODE AND ELECTRODE ASSEMBLY

FIELD OF THE INVENTION

This invention relates generally to a skin conducting electrode and electrode assembly and more particularly to a disposable skin conducting electrode assembly containing a non-linear electrode wire.

BACKGROUND OF THE INVENTION

Transcutaneous electrical nerve stimulation (TENS) is the use of a high frequency electrical stimulation which is applied to an area of the body to relieve pain. In the case of an incision, an electrode is applied to each side of the incision so that small electrical impulses stimulate the nerve area. In many cases, this stimulation greatly reduces or eliminates the pain sensation. The advantage of TENS is that it is a non-invasive and non-narcotic method of managing pain. TENS does not cure or eliminate the cause of the pain, rather it diminishes the feeling of the pain. Thus, with the use of TENS, patients are often able to cough or ambulate more comfortably in situations where normal pain would have precluded this. And because the pain is substantially reduced, narcotic drugs can often be eliminated so that the patient is not drowsy and does not experience the ups and downs of narcotic usage.

There are numerous electrodes in the prior art, some of which have been used for TENS. For instance, in U.S. Pat. No. 3,817,252 to Maurer, an electrode designed for TENS is disclosed which has both a low impedance screen and a diffuser screen beneath a pad. Another body surface electrode, disclosed in U.S. Pat. No. 3,607,788 to Adolph and Bernstein, consists of a liquid electrode which dries on the skin. An electrode consisting of a metal foil body has also been disclosed in U.S. Pat. No. 3,817,253 to Gonser.

A difficulty which has been experienced with prior art electrodes is their lack of stretchability. Often, when a patient moves, the skin to which the electrode is attached stretches. In many cases, this skin stretching either causes the electrode to come loose as the adhesive holding the electrode to the skin breaks away from the skin, or the electrode to break in two. Another difficulty with prior art devices is that they have not been sufficiently flexible. As a result of this, when the patient's body flexes, the electrode has pressure points which create higher current densities in spots. This lack of flexibility also increases the likelihood that the adhesive holding the electrode to the body will break away.

SUMMARY OF THE INVENTION

In accordance with the present invention, a disposable skin conducting electrode assembly and electrode is provided for supplying transcutaneous electrical stimulation to the nerves of a patient. The present invention overcomes difficulties of the prior art by providing an electrode and electrode assembly which can stretch and which can easily flex. In addition, the electrode of the present invention provides good conductivity over a width of skin which is greater than the width of the electrode itself.

In one embodiment of the present invention, the electrode is formed from a thin conductive wire arranged in a flat saw-toothed configuration. This electrode is sandwiched between a gel pad which contacts the skin and an adhesive pad which extends beyond the gel pad and also holds the gel pad and electrode against the skin. A lead wire is attached to the electrode and is designed to be connected with a suitable source of electrical impulses. The saw tooth configuration provides for stress relief and eliminates the tendency of the wire to break when stressed to conform to a body contour.

Other features and advantages of the present invention are related in or apparent from the detailed description of the preferred embodiments of the invention found hereinbelow.

DETAILED DESCRIPTION OF THE PREFERRED EMBODIMENTS

Figure 1:
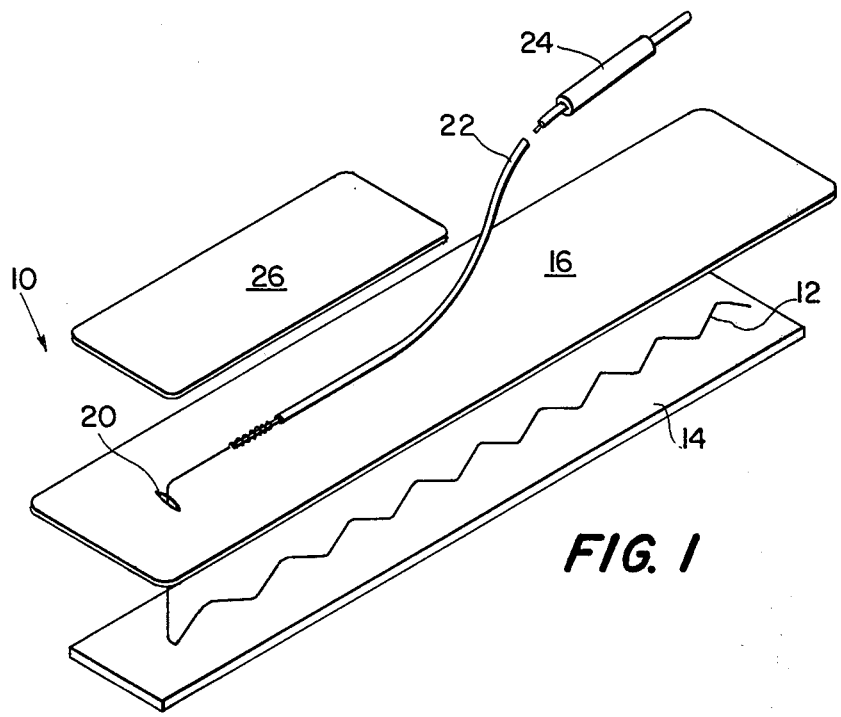
FIG. 1 is an exploded perspective view of the components of the skin conducting electrode assembly in accordance with a preferred embodiment of the present invention.
Figure 2:
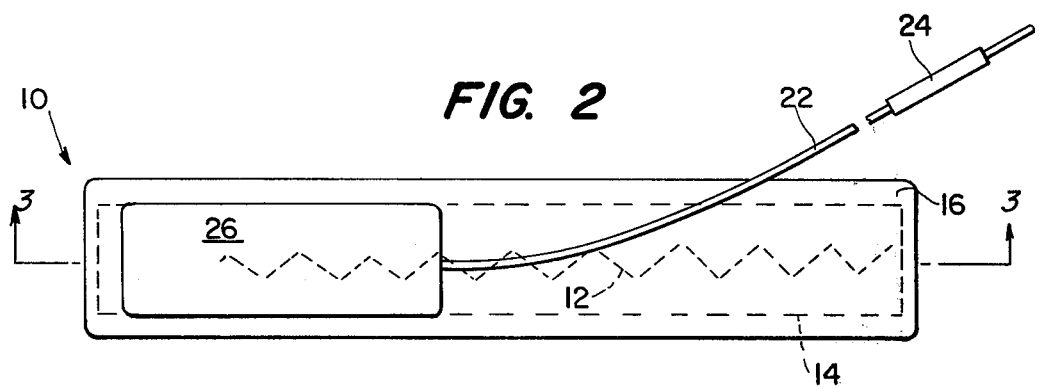
FIG. 2 is a top plan view of the skin conducting electrode assembly showing the hidden components in phantom.
Figure 3:
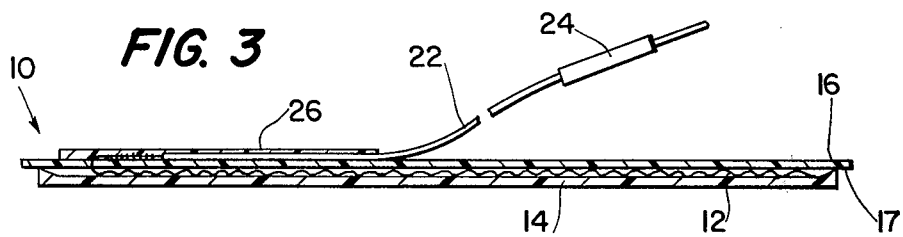
FIG. 3 is a cross-sectional side view of the skin conducting electrode assembly taken along the line 3—3 in FIG. 2.

With reference now to the drawings in which like numerals represent like elements throughout the several views, a presently preferred embodiment of the present invention is depicted in FIGS. 1, 2 and 3 and comprises a disposable skin conducting electrode assembly 10 having an electrode 12 sandwiched between a gel pad 14 and an adhesive pad 16. The underside 17 of adhesive pad 16 is the adhesive side so that both electrode 12 and gel pad 14 adhere to adhesive pad 16. As shown, gel pad 14 is rectangular in shape and it completely covers electrode 12 to prevent direct contact of electrode 12 with the skin of the patient. Adhesive pad 16 is likewise rectangular in shape with rounded corners and is larger than gel pad 14 so that the adhesive underside 17 extends beyond the outer edges of gel pads 14. Electrode 12 extends through a slot 20 near one end of adhesive pad 16 where one end of electrode 12 is soldered to a conductive lead wire 22. Lead wire 22 has a banana plug 24, or other suitable end, to electrically connect electrode 12 with a suitable source of electric impulses. In order to keep lead wire 22 from pulling on electrode 12, an adhesive strip 26 is placed over lead wire 22. Adhesive strip 26 adheres to both lead wire 22 and the top of adhesive pad 16, so that lead wire 22 is held to electrode assembly 10 by adhesive strip 26.

Figure 4:
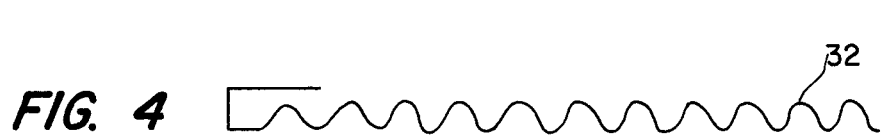
FIG. 4 is a plan view of an alternative embodiment of an electrode used in the skin conducting electrode assembly of the present invention.
Figure 5:
FIG. 5 is a plan view of still another alternative embodiment of an electrode used in the present invention.

As shown in FIGS. 1 and 2, electrode 12 is formed in a saw-toothed shape. Preferably, electrode 12 is a thin conductive wire made of silver, although stainless steel or other conductive materials can also be used. Electrode 12 is formed in a non-linear configuration for two purposes. First, the saw-toothed pattern allows electrode 12 to stretch and flex. Second, a greater area of gel pad 14 lies in close contact to a wire which is so configured, so that there is little voltage drop along the entire area of gel pad 14. Other configurations which are suitable for these purposes are depicted in FIGS. 4 and 5. In FIG. 4, an electrode 32 is shown having a sinusoidal configuration. FIG. 5 depicts an electrode 42 which has a series of overlapping loops.

In operation, skin conducting electrode assembly 10 functions in the following manner when it is used for transcutaneous electrical nerve stimulation of an incision. Usually, two electrode assemblies 10 are placed longitudinally along each side of the incision. Electrode assembly 10 is held to the skin of the patient by the adhesive on the underside 17 of adhesive pad 16. A suitable material for adhesive pad 16 is ⅛ inch thick four pound "White Foam" cross link polythelene material with an applied adhesive selected from a group of adhesives that are medically compatible and are well known in the art. The overlapping edges of adhesive pad 16 holds gel pad 14 and electrode 12 in close contact with the skin of the patient. Gel pad 14 is made from a cellular foam material which is impregnated with an electrolyte gel such as Ringer's solution to provide a low impedance skin contact. After electrode assembly 10 is attached to the patient's skin, lead wire 22 is then connected to a suitable source of electrical impulses by banana plug 24. The electrical impulses travel through wire 25 to electrode 12 and then through the electrolyte solution in gel pad 14 to the patient's skin. The electrical impulses reduce or eliminate pain sensation in the area of the skin near the electrode, and due to the non-linear configuration of the wire of electrode 12, a wide area of the skin receives this stimulation from gel pad 14. As the patient moves, electrode assembly 10 is subject to the flexes and stretches of the skin it is adhered to. Electrode 12 flexes and stretches as well, making the electrode assembly 10 more comfortable to wear and less likely to come loose from the patient. In addition, so-called "hot spots" are reduced as the wire of electrode 12 easily flexes and does not crimp together.

Although the invention has been described in detail with respect to exemplary embodiments thereof, it will be understood by those of ordinary skill in the art that variations and modifications may be effected within the scope and spirit of the invention

I claim:

1. A skin conducting electrode assembly for use in supplying electrical impulses to a patient to reduce pain, said electrode assembly comprising, in combination, an electrode comprising a thin conductive member having an undulating configuration along the length thereof such that said member extends across a width of skin substantially greater than the width of said member; means for providing electrical impulses to said conductive member including a lead wire directly connected to said electrode; a gel pad in contact with one side of said electrode, said gel pad extending beyond the configuration of said member to prevent direct contact of said electrode with the skin of the patient; an adhesive pad in adhesive contact with the other side of said electrode, said adhesive pad extending beyond the outer edges of the gel pad to hold the assembly to the patient and to maintain said gel pad and said electrode in electrical contact with the skin of the patient, the configuration of said conductive member providing a wide area of the skin which is in close contact with said electrode, such that said electrode easily stretches and flexes as the skin or said assembly stretches and flexes, a portion of said conductive member extending through said adhesive pad said lead wire being attached to that portion of said conductive member extending through said adhesive pad and said assembly further comprising an adhesive strip secured to said adhesive pad holding said portion of said conductive member and a portion of said lead wire firmly in place.

2. A skin conducting electrode assembly as claimed in claim 1, wherein the undulating configuration of said conductive member is saw-toothed.

3. A skin conducting electrode assembly as claimed in claim 1, wherein the undulating configuration of said conductive member is sinusoidal.

4. A skin conducting electrode assembly as claimed in claim 1, wherein the undulating configuration of said conductive member comprises a repeating pattern of loops.

5. A skin conducting electrode assembly as claimed in claim 1, wherein said conductive member is made of silver.

* * * * *